United States Patent [19]

Koss

[11] Patent Number: 4,541,427

[45] Date of Patent: Sep. 17, 1985

[54] SURGICAL INSTRUMENT ASSEMBLY

[76] Inventor: Walter Koss, Industriestrasse, 6222 Geisenheim, Fed. Rep. of Germany

[21] Appl. No.: 507,693

[22] Filed: Jun. 24, 1983

[30] Foreign Application Priority Data

Jun. 28, 1982 [DE] Fed. Rep. of Germany ... 8218440[U]

[51] Int. Cl.$^4$ .............................................. A61F 17/32
[52] U.S. Cl. ............................ 128/305.3; 128/207.14; 604/116
[58] Field of Search ................ 128/305.3, 305, 207.14, 128/207.15, 207.16, 207.17; 604/116

[56] References Cited

U.S. PATENT DOCUMENTS

| | | | |
|---|---|---|---|
| 2,991,787 | 7/1961 | Shelden et al. | 128/305.3 X |
| 3,182,663 | 5/1965 | Abelson | 128/305.3 |
| 4,192,312 | 3/1980 | Wilson | 128/305 X |

*Primary Examiner*—William H. Grieb
*Attorney, Agent, or Firm*—Gifford, Van Ophem, Sheridan, Sprinkle & Nabozny; Gifford, Van Ophem, Sheridan, Sprinkle & Nabozny

[57] ABSTRACT

A surgical instrument assembly for making a shunt passage between the oesophagus and the surface of the neck, for accommodating a larynx prosthesis. The assembly includes a curved puncture needle, a prosthesis place holder and a placing needle, and optionally includes a tracheostoma template. The bent configuration of the puncture needle ensures correct formation of the shunt passage. The prosthesis place holder allows the shunt passage to heal up in the correct configuration. The placing needle provides for correct fitting and radiological checking of the place holder.

19 Claims, 8 Drawing Figures

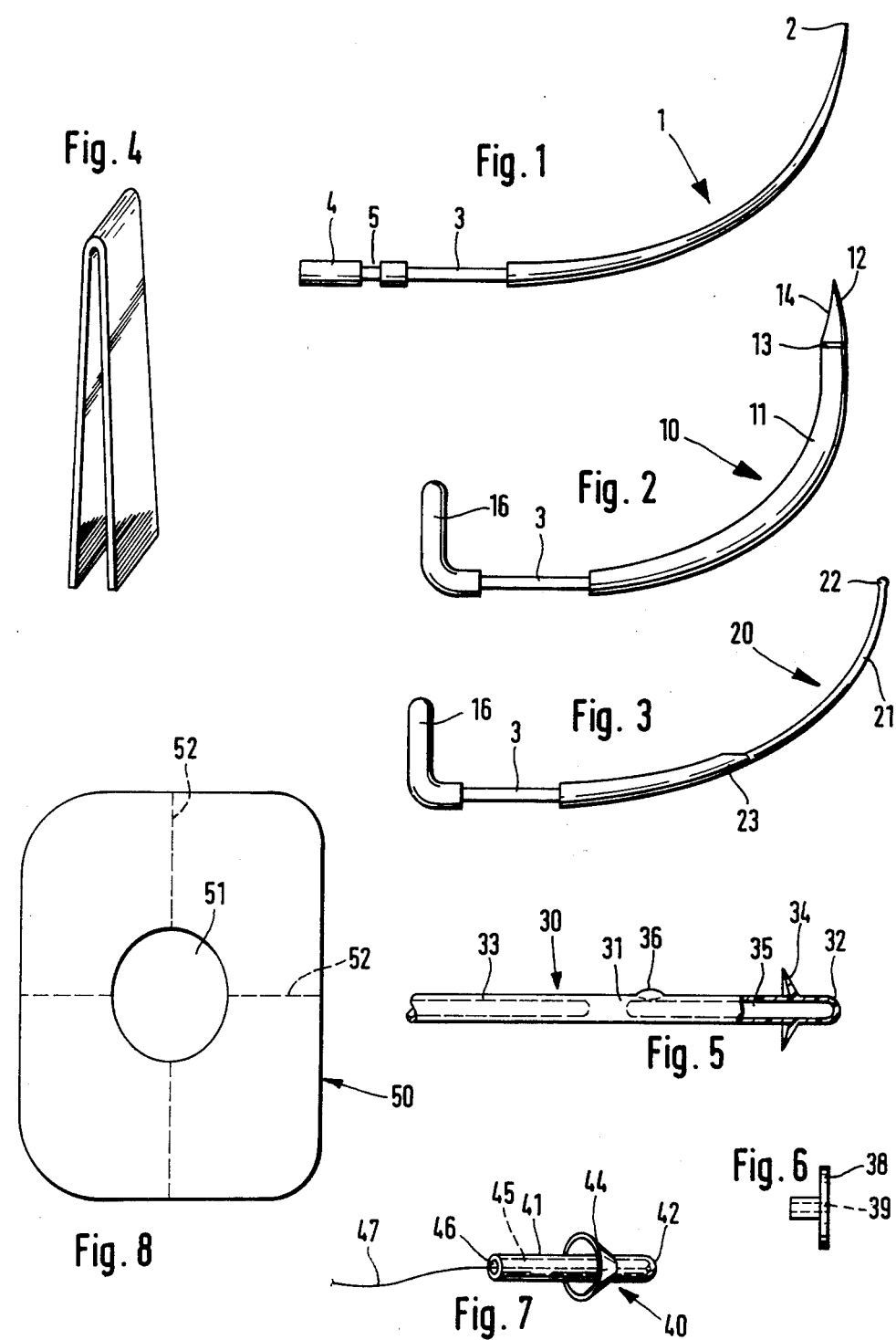

SURGICAL INSTRUMENT ASSEMBLY

BACKGROUND OF THE INVENTION

I. Field of the Invention

The invention relates to a surgical instrument for making a space for receiving a larynx prosthesis.

II. Description of the Prior Art

When a cancer is found in the region of the larynx, the cancer is removed, sometimes together with parts of the air pipes and the alimentary passage, whereafter an air intake and discharge opening (tracheostoma) is formed in the neck. In order to provide the patient with the facility for speech, a connecting passage, which may be referred to as a shunt passage, is formed between the tracheostoma and the alimentary passage, after it has been ensured that mucous membrane folds which are capable of vibrating are to be found above the shunt passage in what remains of the alimentary passage, or the substitute therefor. The shunt passage serves as a space for receiving a larynx prosthesis which may comprise a pipe with a cap-like end and a slot disposed therein, to act as a valve. By closing the tracheostoma, the patient can pass respiration air by way of the larynx prosthesis into the alimentary passage and the mouth-throat cavity, which enables him to achieve natural speech relatively quickly or after some practice.

Hitherto, the instrument used for making the shunt passage for the larynx prosthesis has been a puncture needle with which a puncture is made from the tracheostoma to the alimentary passage, whereupon a vein catheter is passed through the puncture needle and taken through the nose, by means of an oesenoesophagoscope. A hose or tube is pulled through with the vein catheter, the hose being passed through the punctured passage and through the nose and the ends thereof being knotted together. It is possible to use a tube like puncture needle having a passage for pulling through a thread, such needle being referred to as a Braunule instrument.

A further known operating technique is cutting with a pointed scalpel towards a blind fitted rubber catheter, whereupon a hose is fitted into the cut (shunt), as a place holder.

For reasons of voice formation and in order to avoid leakage air passing into the stomach, it is desirable for the larynx prosthesis not to face downwardly with its slotted end. Such a positioning is achieved with the operating technique first referred to above, because, during the healing process, the hose which is introduced plays the part of a place holder for the larynx prosthesis and does not have any downward tendency. A disadvantage however is that the hose which is passed through the mouth cavity and the hose has a detrimental effect on the patient (traumatisation, a nuisance and a strain during the healing process, and dysphagia).

SUMMARY OF THE PRESENT INVENTION

The novel surgical instrument assembly seeks to achieve the object of making the cavity for receiving the larynx prosthesis, at or after amputation of the larynx, without requiring a hose or tube to be passed through the nose, wherein the receiving cavity is curved upwardly.

According to the invention, the instrument assembly comprises a puncture needle, a prosthesis place holder and a placing needle. The puncture needle is curved or bent so that the use thereof results in a curved or bent connecting passage. The prosthesis place holder is of a form which substantially corresponds to the subsequent prosthesis and can be secured in the punctured passage, more specifically, on repeated occasions, as is desirable during postoperative treatment. In order to reduce mental and emotional strain, the patient is fitted with the larynx prosthesis at a relatively early stage, but that must be replaced by the place holder if swelling occurs, such as after irradiation. Provided in the place holder is a guide passage or channel which can be used to accommodate the placing needle so that the placing needle correctly fits the prosthesis place holder in place, and possibly to provide for radiological monitoring.

The cross-sectional diameter of the puncture needle corresponds to the cross-section of the subsequent larynx prosthesis and is for example 4 to 5 mm. Depending on the operative factors, the puncture needle is applied from the outside inwardly or from the inside outwardly, the latter procedure being used in the course of the larynx operation, during which such access is possible. When the shunt passage is formed after the larynx operation, the puncture is made from the outside inwardly and the point of the puncture needle, which goes into the alimentary passage, is observed with an oesphago-endoscope. In order to be able to establish the correct degree of penetration, the puncture needle has a marking means at the transition between the point and the bent or curved central portion. The same applies, if the tip of the puncture needle has a hollow groove-like flattened portion at the inward side, in which case the resistance to puncturing is additionally reduced. In order to avoid lesions, the puncture needle should not have any cutting edge.

So that the puncture needle can be grasped, provided thereon is a flattened portion to which a handling clip or 'guide means' is fitted. It is also possible to provide a hooked end portion for the purpose of gripping the puncture needle. So that a hose or pipe can be drawn through the punctured passage with the puncture needle, the unpointed end of the puncture needle has a cylindrical portion with a peripheral groove therein, the hose or pipe being pushed over the cylindrical portion and the edge thereof engaging into the groove. The puncture needle, of such a configuration, is used in particular for puncturing from the inside outwardly.

The prosthesis place holder comprises silicone rubber, at least in its outer wall portions. That material has a very high level of breaking or tensile strength, as long as it has no surface damage. The guide passage with opening is produced by casting or moulding the place holder in a mould. That mode of production provides an undamaged surface.

The placing needle is of a bent or curved shape which is substantially the same as the bent or curved configuration of the puncture needle. In order to avoid damaging the prosthesis place holder, which comprises silicone rubber, the placing needle has a front end portion which is of increased thickness. It is also possible for the placing needle to be in the form of part of the place holder, in other words, for it to be left in the silicone rubber prosthesis place holder, and for the projecting end of the placing needle to be used for securing purposes.

BRIEF DESCRIPTION OF THE DRAWING

An embodiment of the invention will now be described in greater detail with reference to the accompanying drawings in which:

FIG. 1 shows a puncture needle,
FIG. 2 shows another puncture needle,
FIG. 3 shows a placing needle,
FIG. 4 shows a handling clamp means,
FIG. 5 shows a prosthesis place holder,
FIG. 6 shows an accessory member therefor,
FIG. 7 shows another prosthesis place holder, and
FIG. 8 shows a tracheostoma template.

DETAILED DESCRIPTION OF THE PREFERRED EMBODIMENT OF THE PRESENT INVENTION

It may be noted that, in connection with tracheostomy, it should be desirable to maintain a uniform stoma size. Use is made for that purpose of a tracheostoma template 50 (as shown in FIG. 8) of 75 mm to 55 mm in size, with an oval opening 51 of 25 to 20 mm. The template 50 is about 3 mm in thickness and comprises elastomeric silicone which has good adhesion to the skin. The area of the operation can be marked on the neck of the patient by means of the edges of the template 50 and with additional markings 52.

Referring now to FIG. 1, shown therein is a puncture needle which is about 13 cm in length, for the glottoplasty. The puncture needle 1 comprises stainless steel and is curved, starting from a tip 2 to a flattened portion 3 (having two holding or gripping surfaces which are parallel to each other). The cross-section of the needle, which is in other respects round, increases to about 4 mm. On the side of the flattened portion 3, which is remote from the point 2, the needle 1 has a cylindrical end portion 4 in which there is an annular groove 5. A hose or tube can therefore be pushed on to the end portion 4, with the end edge of the hose engaging into the groove 5 and thus not causing difficulty by projecting above the surface of the needle, when the hose or tube is drawn through a punctured passage (shunt passage). The punctured passage (shunt passage) is bent or curved, by virtue of the curved configuration of the needle 1. In order to facilitate handling the needle 1, use is made in that connection of a handling clamp or clip member or 'guide means', as shown in FIG. 4, which is fitted to the flattened portion 3, and which clamps the needle 1 firmly between the parallel holding surfaces.

Reference will now be made to FIG. 2 showing a further puncture needle which is suitable in particular for forming a shunt passage subsequent to the larynx operation. The needle 10 comprises a pin member which is about 14 cm in length and which comprises stainless steel. The needle 10 has a bent or curved middle portion 11 and a tapering tip or point 12, of about 15 mm in length. The point or tip 12 is separated from the middle region 11 by a clearly visible marking 13 which may comprise an annular groove or notch. The tip or point 12 is of round cross-section. It is also possible, however, for a hollow groove-like flattened portion to be provided at the inward side 14. However, the tip or point 12, like the middle portion 11, should not have any cutting edge. The diameter of the middle portion 11 corresponds to the diameter of the prosthesis to be fitted, and is for example 5 mm. Disposed at a position adjoining the middle portion 11 is a flattened portion 3 which serves for mounting the holding clip or clamp member shown in FIG. 4. The needle may also have a bent end portion as indicated at 16, which can also serve for handling the needle.

FIG. 3 shows a placing needle 20, the external configuration of which broadly corresponds to the puncture needle 1 or 10 but which is thinner in the middle region 21 and which has a rounded end portion 22. The rounded end portion 22 is of increased thickness and is from 3 to 3.5 mm in diameter, while the diameter of the portion 21 is 2 mm. For reasons of stability, the middle portion 21 may increase in thickness in a rearward direction, as indicated at 23; however, care should be taken to ensure that the portion 21 is of sufficient length, so that a place holder which is pushed on to the placing needle does not jam at 23. The flattened portion 3 and the bent end portion 16 have already been described above.

The handling clip or clamp or guide member as shown in FIG. 4 is known per se and therefore does not need to be described in detail herein.

Referring to FIG. 5, shown therein is a prosthesis place holder 30 comprising an elastomer, for example silicone rubber (Medical Grade). It comprises a cylindrical main body portion 31 which is about 4 cm in length and which has a rounded end at 32 and which can continue in a hose or tube portion 33. Disposed at a spacing of about 6 to 9 mm from the rounded end 32 is a plate-like or disc-like, spreadable, soft, compressible securing portion 34 which is made integrally with the main body portion 31. Disposed in the interior of the main body portion 31 is a guide passage or channel 35 which opens sideways to the exterior, by way of a radial opening 36. With the mode of manufacture employed in this respect, the guide passage or channel 35 terminates just behind the opening 36. It is also possible, however, for the guide passage 35 to continue in the interior of the tube portion 33. When producing the place holder from silicone rubber, care must be taken to ensure that the surface is in no way damaged, so that the radial opening 36 is not perforated, but is produced with a reinforced or strengthened edge portion when casting or injection moulding the member 30.

Another disc-like securing portion 38 (see FIG. 6) with an aperture 39 therethrough can be pushed over the tube portion 33 on to the main body portion 31 and, in conjunction with the disc-like portion 34, serves to secure the holder 30 to the wall of the alimentary passage or the wall of the windpipe of the patient.

FIG. 7 shows another embodiment of a prosthesis place holder 40 which comprises a cylindrical main body portion 41 which is 25 mm (or more) in length and which has a rounded end at 42 and a guide passage 45. Vulcanised into the end 42 is a thread 47 which extends outwardly through the guide passage 45 and an opening 46, and which may be about 30 cm in length. The holder 40 includes a plate-like portion 44 corresponding in arrangement to the securing portion 34 in the embodiment indicated at 30 in FIG. 5.

The puncture needle 1 is used in the course of the larynx operation if, by virtue of the neck area being opened, it is possible to make a cut or puncture from the inside outwardly to form the receiving cavity (shunt) for the larynx prosthesis. Before that, the tube portion 33 of the prosthesis place holder 30 or the portion 41 of the place holder 40 is pushed on to the end portion 4 until the edge of the tube or hose disappears into the peripheral groove 5. When the needle 1 is drawn outwardly through the wall of the alimentary passage and the rear wall of the windpipe, the place holder 30 or 40 can be drawn to the correct position, until the plate-like securing portion 34 or 44 comes to bear against the front wall of the alimentary passage or oesophagus. After the needle 1 has been withdrawn from the tube portion 33 or 41 respectively, the outwardly projecting end 33 or 41 of the place holder 30 or 40 is secured to the neck of the patient. The second plate-like securing portion 38 can be later pushed over the tube portion 33 and the main body portion 31 or 41 in order comfortably to secure the holder 30 to the neck of the patient. The aperture 39 through the plate-like member 38 is of correspondingly narrow size so as to produce a clamping or locking action on the main body portion 31 or 41. The opening 36 or 46 is accessible from the exterior after implantation of the place holder 30 or 40 and the guide passage 35 or 45 can be filled with the placing needle 20 if the location and fit of the place holder is to be checked by X-ray means.

The puncture needle 10 is intended for the subsequent formation of the shunt, after the patient has healed up from the larynx amputation operation. In that case, a puncture is made from the tracheostoma which has been made, towards the alimentary passage, the tip or point 12 which issues from the wall of the alimentary passage being observed and monitored by means of an oesphago-endoscope. By virtue of the curved configuration of the puncture needle 10, the point or tip 12 extends substantially parallel to the longitudinal extent of the alimentary passage, if the puncture was properly made. The degree of penetration can be detected by means of the marking 13 and the flattened portion 14.

After the puncture needle 10 has been removed from the pierced opening or passage, the holder 30 or 40 is fitted, and for that purpose is drawn on to the placing needle 20. To do that, the rounded end 22 is fitted by way of the opening 36 or 46 into the interior of the holder 30, and the latter is pulled tight. The holder 30 then assumes a curved configuration, as corresponds to the prosthesis in its finished form, but is thinner because of the pulling force applied thereto, so that the spreadable securing member 34 can be folded together or collapsed down to a relatively small size when the assembled structure comprising the components 20 and 30, or 40, is implanted into the passage or shunt produced. When the place holder has passed into the cavity of the alimentary passage, the plate-like securing portion 34 or 44 springs back into its initial position, and spreads out. After the placing needle has been withdrawn, the securing portion 38 is pushed into place. It will be appreciated that the holder 30 or 40 may also be additionally secured in another suitable manner.

As, in regard to the placing needle, it is essentially the portions 21 and 22 thereof that are important, it is possible for the other parts thereof to be omitted. A placing means, of that kind of reduced construction, can be left in the place holder 30 or 40, to impart stability in respect of shape thereof. By virtue of being made of metal, the placing means also serves as a contrasting means for X-ray investigation. It will be appreciated that in this case also the place holder is additionally secured externally on the neck, without the position of the shunt-being at an inclined angle upwardly-being detrimentally affected thereby.

The holder 30 or 40 projects with its end 32 or 42 respectively, into the oesophagus, and, with its portion 34 or 44 serving as a screening or shield means, closes off the shunt passage which otherwise forms a communication between the oesophagus and the windpipe. That therefore prevents food from getting into the respiratory tract.

What is claimed is:

1. A surgical instrument assembly for making a cavity for receiving a larynx prosthesis, comprising:
   a curved puncture needle,
   said needle having a tip at one end, a curved central portion and a gripping means at the other end;
   a prosthesis place holder,
   said place holder comprising an elastomer having a main cylindrical body portion, a compressible securing portion disposed thereon, and a guide passage extending within said main body portion and being accessible from the exterior through an opening, and
   a placing needle,
   said placing needle having a rounded end portion, a curved shank portion and a grip means at the other end.

2. An assembly according to claim 1 wherein said puncture needle has a diameter of about 4 to 5 mm.

3. An assembly according to claim 1 wherein said puncture needle has an annular marking means at the transition between said tip portion and said curved central portion.

4. An assembly according to claim 1 wherein said tip portion of said puncture needle has a hollow-like flattened portion at its inwardly facing side.

5. An assembly according to claim 1 wherein said gripping means on said puncture needle includes a flattend portion for fitting a handling clip means thereto.

6. An assembly according to claim 1 wherein said gripping means of said puncture needle has means for receiving and clampingly retaining a tube member thereon.

7. An assembly according to claim 1 further comprising a securing means, said securing means being adapted to be fitted on said prosthesis place holder.

8. An assembly according to claim 1 wherein said prosthesis place holder comprises silicone rubber.

9. An assembly according to claim 8 wherein said prosthesis holder is produced by casting in a mould.

10. An assembly according to claim 1 wherein said curved shank portion of said placing needle is of a curved configuration corresponding to said puncture needle.

11. An assembly according to claim 1 wherein said rounded end portion of said placing needle is of increased thickness.

12. An assembly according to claim 1 further comprising a tracheostoma template means.

13. An assembly according to claim 1, wherein said puncture needle is characterized in that is possesses no cutting edge.

14. An assembly according to claim 1, wherein said guide passage is closed at a location spaced from said opening.

15. An assembly according to claim 14, wherein said opening is disposed at an end of said prosthesis place holder.

16. An assembly according to claim 1, wherein said opening is disposed at an end of said prosthesis place holder.

17. An assembly according to claim 1, wherein said compressible securing portion comprises a flared portion abuttable against the interior wall of the alimentary passage of a patient.

18. A method for making a cavity in a patient's throat for receiving a larynx prosthesis therein, comprising the steps of:

forming a curved puncture in said patient's throat by puncturing said throat with a curved puncture needle; said needle having a tip at one end, a curved central portion and a gripping means opposite said one end; and securing a prosthesis place holder in said curved throat puncture; said place holder comprising an elastomer having a main cylindrical body portion, a compressible securing portion disposed thereon, and a guide passage extending within said main body portion and being accessible from the exterior through an opening therein;

wherein said securing step is carried out by: (a) engaging said place holder with a placing needle, said placing needle comprising a rounded end portion, a curved shank portion and a grip means opposite said rounded end portion; (b) placing said engaged placing needle and place holder in said curved throat puncture; and (c) disengaging said placing needle from said place holder, and withdrawing said placing needle from said throat puncture.

19. The method according to claim 18, wherein said puncture step is carried out so as to avoid forming lesions in said throat puncture by employing a puncture needle in said puncture step which is characterized by possessing no cutting edge; and wherein said securing step is carried out using a place holder wherein said guide passage is closed at a location spaced from said opening, said place holder and said placing needle being engaged by insertion of said rounded end portion of said placing needle through said opening into said guide passage.

* * * * *

UNITED STATES PATENT AND TRADEMARK OFFICE
CERTIFICATE OF CORRECTION

PATENT NO. : 4,541,427
DATED : September 17, 1985
INVENTOR(S) : Walter Koss

It is certified that error appears in the above-identified patent and that said Letters Patent are hereby corrected as shown below:

Col. 1, line 54, delete "hose" and insert --nose--.

Signed and Sealed this

Twenty-eighth Day of October, 1986

[SEAL]

Attest:

DONALD J. QUIGG

*Attesting Officer*    *Commissioner of Patents and Trademarks*